(12) United States Patent
Cho et al.

(10) Patent No.: US 8,579,824 B2
(45) Date of Patent: Nov. 12, 2013

(54) METHOD AND APPARATUS TO MONITOR CHANGE IN INSPIRATORY EFFORT USING INTRATHORACIC BLOOD PRESSURE WAVEFORM MORPHOLOGY

(75) Inventors: Yong K. Cho, Maple Grove, MN (US); Mark K. Erickson, Brooklyn Park, MN (US); Todd M. Zielinski, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 1048 days.

(21) Appl. No.: 12/609,688

(22) Filed: Oct. 30, 2009

(65) Prior Publication Data

US 2011/0105858 A1 May 5, 2011

(51) Int. Cl.
*A61B 5/02* (2006.01)
(52) U.S. Cl.
USPC .......................... 600/483; 600/301; 600/529
(58) Field of Classification Search
USPC ......................................... 600/301, 483, 529
See application file for complete search history.

(56) References Cited

U.S. PATENT DOCUMENTS

| | | | |
|---|---|---|---|
| 4,982,738 A | 1/1991 | Griebel | |
| 6,021,352 A | 2/2000 | Christopherson et al. | |
| 6,141,590 A | 10/2000 | Renerie | |
| 6,213,955 B1* | 4/2001 | Karakasoglu et al. | 600/529 |
| 6,368,287 B1* | 4/2002 | Hadas | 600/529 |
| 6,881,192 B1* | 4/2005 | Park | 600/529 |
| 7,179,229 B1 | 2/2007 | Koh | |
| 7,225,021 B1 | 5/2007 | Park | |
| 2004/0210261 A1 | 10/2004 | King et al. | |
| 2005/0039745 A1 | 2/2005 | Stahlman et al. | |
| 2008/0009755 A1* | 1/2008 | Patangay et al. | 600/484 |
| 2008/0058892 A1 | 3/2008 | Haefner et al. | |
| 2008/0146893 A1 | 6/2008 | Levendowski | |
| 2009/0240126 A1 | 9/2009 | Baker, Jr. | |

FOREIGN PATENT DOCUMENTS

WO 2008118951 10/2008

OTHER PUBLICATIONS (PCT/US2010/053194) PCT Notification of Transmittal of the International Search Report and the Written Opinion of the International Searching Authority, Mailed Jan. 3, 2011, 11 pages.
Dursunoglu, N. Effects of CPAP on right ventricular myocardial performance index in obstructive sleep apnea patients without hypertension. Respiratory Research. 2006; p. 22, vol. 7(1).
Naughton MT. The link between obstructive sleep apnea and heart failure: Underappreciated opportunity for treatment. Curr. Cardio. Rep. 2005; pp. 211-215, vol. 7(3).

* cited by examiner

*Primary Examiner* — Navin Natnithithadha
*Assistant Examiner* — Etsub Berhanu
(74) *Attorney, Agent, or Firm* — Michael C. Soldner (57) ABSTRACT

An implantable medical device and associated method detect obstructed inspiration by monitoring an blood pressure signal. A respiration signal is monitored and a phase of respiratory inspiration is detected from the respiration signal. A trend in the pressure signal is measured during the inspiration phase. Obstructed inspiration for the inspiration phase is detected in response to the measured the trend.

21 Claims, 4 Drawing Sheets

METHOD AND APPARATUS TO MONITOR CHANGE IN INSPIRATORY EFFORT USING INTRATHORACIC BLOOD PRESSURE WAVEFORM MORPHOLOGY

TECHNICAL FIELD

The present disclosure relates generally to implantable medical devices and, in particular, to an implantable medical device system and method for monitoring a patient's inspiratory effort for detecting obstructed inspiration.

BACKGROUND

Respiration monitoring is useful in diagnosing and managing pathological conditions. Obstructive sleep apnea (OSA) is a risk factor for the development of systemic hypertension, ischemic heart disease and congestive heart failure. OSA is also associated with an increased risk of cardiovascular morbidity and mortality. However, sleep apnea remains largely undiagnosed and untreated. Discrimination between obstructive sleep apnea and central sleep apnea can be challenging and generally requires a sleep study, which is costly and burdensome to the patient. Continuous positive airway pressure (CPAP) has been found to be beneficial in reducing blood pressure, decreasing cardiac arrhythmias, and improving left ventricular function and reducing the incidence and mortality of cardiovascular diseases. Despite the availability of an effective therapy the majority of patients experiencing OSA go underdiagnosed and untreated. There remains a need, therefore, for monitoring respiration in patients to diagnosing and monitoring respiratory conditions such as in OSA or other respiratory diseases such as asthma, chronic obstructive pulmonary disease (COPD), emphysema, or congestive heart failure.

DETAILED DESCRIPTION

In the following description, references are made to illustrative embodiments. It is understood that other embodiments may be utilized without departing from the scope of the disclosure. In some instances, for purposes of clarity, the same reference numbers may be used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Various embodiments described herein utilize an intrathoracic blood pressure signal for the detection of increased inspiratory effort which may be associated with obstructed inspiration such as in OSA, asthma, COPD, emphysema, congestive heart failure, or other disease conditions. As used herein, the term "intrathoracic blood pressure signal" includes any blood pressure signal measured within the thoracic cavity. Such blood pressure signals include, for example, a pressure signal measured within a cardiac chamber (atrial or ventricle), also referred to herein as an "intracardiac pressure signal", and pressure signals measured in a blood vessel within the thorax of the patient, e.g. the vena cava, the pulmonary artery, etc.

It is contemplated that extrathoracic blood pressure measurements could be substituted for intrathoracic blood pressure measurements in the methods described herein. Since intrathoracic pressure decreases during inspiration, intrathoracic blood pressure reflects that decrease during the inspiration phase. With increased inspiratory effort due to obstructed airways, the decrease in intrathroacic blood pressure becomes greater or exaggerated. Extrathoracic blood pressure signals also tend to be modulated by respiration and could potentially be used for detecting changes during the inspiration phase that are indicative of increased inspiratory effort. Extrathoracic blood pressure signals may include, but are not limited to, arterial blood pressure signals in the neck, abdomen or limbs. It is recognized that the change in blood pressure due to changes in inspiratory effort may present differently in an extrathoracic blood pressure signal than in an intrathoracic blood pressure signal. For example, in the abdomen, abdominal cavity pressure may increase during inspiration, causing an increase in the blood pressure signal in proportion to inspiratory effort rather than a decrease as in the thoracic cavity. As such, the criteria for detecting increased inspiratory effort based on decreasing trends in intrathoracic blood pressure measurements may be reversed or otherwise adjusted appropriately depending on the location the blood pressure measurement is being taken.

The use of a blood pressure signal for monitoring respiration enables obstructed inspiration detection to be incorporated in an implantable monitoring device that already includes a blood pressure sensor. For example, an implantable medical device that includes hemodynamic monitoring for use in a heart failure patient may include a pressure sensor positioned in a heart chamber or blood vessel. Respiration monitoring for detection of OSA using the blood pressure signal may be incorporated in the hemodynamic monitoring device without requiring additional sensors, leads, or circuitry. Respiration measurements correlated to inspiratory effort and used to detect obstructed inspiration for OSA detection as described herein may similarly be used for detecting increased inspiratory effort associated with other respiratory ailments such as asthma, COPD, emphysema, or congestive heart failure.

Figure 1:
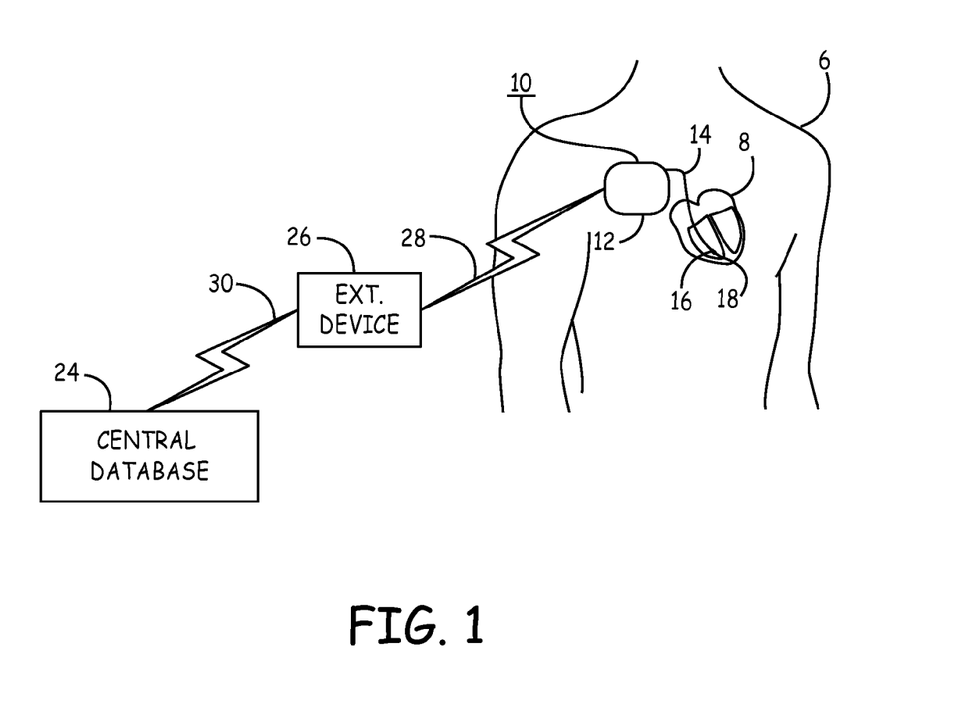
FIG. 1 is a schematic diagram of an implantable medical device coupled to a lead positioned within a patient's heart.

FIG. 1 is a schematic diagram of a patient monitoring system including an implantable medical device (IMD) 10 coupled to a lead 14 positioned within a heart 8 in a patient's body 6. IMD 10 is at least capable of monitoring physiological signals and may or may not include therapy delivery capabilities. IMD 10 may correspond to a variety of implantable medical devices including a cardiac pacemaker, implantable cardioverter defibrillator, implantable hemodynamic monitor, a drug pump, a neurostimulator or the like. Accordingly, IMD 10 may be coupled to additional leads and/or catheters operatively positioned relative to the patient's heart 8 or other body tissues for deploying stimulating/sensing electrodes, other physiological sensors, and/or drug delivery ports. While lead 14 is shown terminated within the right ventricle of the patient's heart, it is recognized that lead 14 may be configured as a transvenous lead that extends into other heart chambers or blood vessels for positioning electrodes and/or physiological sensors in a desired location.

In one embodiment, IMD 10 corresponds to an implantable hemodynamic monitor capable of sensing and recording ECG signals and intracardiac blood pressure signals and storing cardiac electrical and hemodynamic data. ECG signals are sensed using one or more electrodes 18 carried by lead 14 or using alternative electrodes (not shown) incorporated on the hermetically-sealed housing 12 of IMD 10. Housing 12 encloses circuitry (not shown) included in IMD 10 for controlling and performing device functions and processing sensed signals.

Lead 14 is further provided with a pressure sensor 16. Pressure sensor 16 is used for monitoring pressure within the right ventricle. Pressure signals may be monitored for determining metrics of hemodynamic function useful in monitoring heart failure status or diagnosing cardiac dysfunction. In embodiments described herein, the right ventricular intracardiac pressure signal obtained from sensor 16 is further used to derive measurements corresponding to respiratory effort and useful in detecting obstructed inspiration, e.g. as in OSA, as well as a lack of inspiratory effort or severely diminished inspiratory effort associated with central sleep apnea (CSA) or hypopnea, respectively.

While respiration monitoring combined with hemodynamic monitoring in a heart failure patient is one application in which detection of obstructed inspiration can be useful, it is recognized that additional clinical applications will exist in which respiration monitoring using a blood pressure signal for measuring inspiratory effort will be beneficial. For example, methods described herein may be implemented in an implantable device used for diagnosing sleep apnea in non-heart failure patients as well as detecting worsening (or improving) respiratory conditions or events in patients having asthma, emphysema, COPD, or the like.

IMD 10 is capable of bidirectional communication with an external device 26 via telemetry link 28. External device 26 may be embodied as a programmer used to program the operating mode and various operational parameters of IMD 10 as well as interrogate IMD 10 to retrieve data stored by IMD 10. Stored data may include data related to IMD function determined through automated selfdiagnostic tests as well as physiological data acquired by IMD 10 using pressure sensor 16 and electrode(s) 18.

External device 26 is further shown in communication with a central database 24 via communication link 30, which may be a wireless or hardwired link. Programming data and interrogation data may be transmitted via link 30. Central database 24 may be a centralized computer or a web-based or other networked database used by a clinician for remote monitoring and management of patient 6. Various methods described herein and executed for deriving a respiration signal from a pressure signal, detecting breath cycles and deriving various respiration metrics may be implemented in one or more of the IMD system components shown in FIG. 1, namely in the IMD 10, programmer 26 and/or central database 24, and may include any combination of hardware, firmware and/or software. External device 26 may be embodied as a clinic-based programmer having full IMD programming and interrogation functionality or a home-based monitor having interrogation and perhaps limited programming functionality and used for remote patient monitoring. It is recognized that other external devices, such as other physiological monitoring devices or other types of programming devices, may be used in conjunction with IMD 10 and incorporate portions of the methods described herein.

In alternative embodiments, external device 26 may be an external monitor or therapy delivery device, such as a Continuous Positive Airway Pressure (CPAP) device configured to treat obstructive sleep apnea. In some embodiments, IMD 10 may transmit data to external device 26 for use in controlling an apnea therapy delivered by external device 26.

Figure 2:
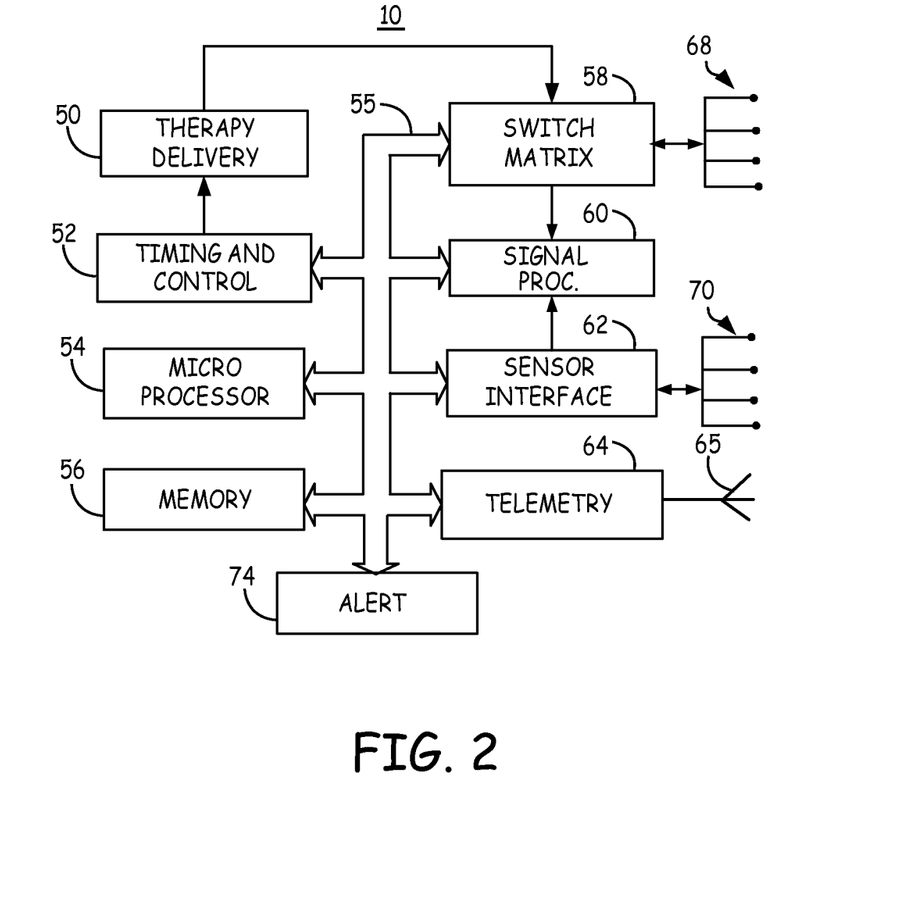
FIG. 2 is a functional block diagram of one embodiment of the IMD shown in FIG. 1.

FIG. 2 is a functional block diagram of one embodiment of IMD 10. IMD 10 generally includes timing and control circuitry 52 and an operating system that may employ microprocessor 54 or a digital state machine for timing sensing and therapy delivery functions (when present) in accordance with a programmed operating mode. Microprocessor 54 and associated memory 56 are coupled to the various components of IMD 10 via a data/address bus 55.

IMD 10 may include therapy delivery module 50 for delivering a therapy in response to determining a need for therapy, e.g., based on sensed physiological signals. Therapy delivery module 50 may provide drug delivery therapies or electrical stimulation therapies, such as cardiac pacing therapy or neurostimulation. Therapies are delivered by module 50 under the control of timing and control circuitry 52. In some embodiments, a therapy may be delivered to treat OSA in response to detecting obstructed inspiration. Such therapies may include electrical stimulation of excitable tissue along the upper airway, such as stimulation of the hypoglossal nerve, or sending control signals to a CPAP device or other external obstructive sleep apnea therapy delivery device. The therapy delivery module 50 may provide a therapy for treating CSA or hypopnea. For example, when a lack of inspiratory effort is measured, phrenic nerve stimulation may be delivered to restore respiration.

Additionally or alternatively, therapies may be delivered to provide cardiac support to counteract the cardiac risks associated with sleep apnea. For example, cardiac resynchronization therapy, vagal nerve stimulation, or drug delivery may be provided in response to detecting OSA to improve cardiac function.

Therapy delivery module 50 is typically coupled to two or more electrode terminals 68 via an optional switch matrix 58. Switch matrix 58 may be used for selecting which electrodes and corresponding polarities are used for delivering electrical stimulation pulses. Terminals 68 may be coupled to connectors providing electrical connection to electrodes incorporated in IMD housing 12 or other lead-based electrodes, including electrode(s) 18 carried by lead 14 (shown in FIG. 1).

Electrode terminals 68 are also used for receiving cardiac electrical signals through any unipolar or bipolar sensing configuration. Cardiac electrical signals may be monitored for use in diagnosing or managing a patient condition or may be used for determining when a therapy is needed and controlling the timing and delivery of the therapy. When used for sensing, electrode terminals 68 are coupled to signal processing circuitry 60 via switch matrix 58. Signal processor 60 includes sense amplifiers and may include other signal conditioning circuitry and an analog-to-digital converter. Electrical signals may then be used by microprocessor 54 for detecting physiological events, such as detecting and discriminating cardiac arrhythmias. Cardiac electrical signals received from terminals 68, which may be intracardiac EGM signals, far field EGM signals, or subcutaneous ECG signals, may be used in one embodiment for determining a heart rate. The heart rate may be used in performing heart rate dependent filtering of a blood pressure signal for deriving a respiration signal.

IMD 10 is additionally coupled to one or more sensors of physiological signals via sensor terminals 70. Physiological sensors include a pressure sensor 16 as shown in FIG. 1 and may further include accelerometers, flow sensors, blood chemistry sensors, activity sensors, postures sensors, or other physiological sensors known for use with implantable devices. Physiological sensors may be carried by leads extending from IMD 10 or incorporated in or on the IMD housing 12.

Signals received at sensor terminals 70 are received by a sensor interface 62 which provides sensor signals to signal processing circuitry 60. Sensor interface 62 receives the sensor signal and may provide initial amplification, filtering, rectification, or other signal conditioning. Sensor signals are used by microprocessor 54 for detecting physiological events or conditions. In particular, signals from pressure sensor 16 are processed by signal processor 60 and/or microprocessor 54 for deriving respiration monitoring parameters therefrom. A respiration monitoring algorithm may be stored in memory 56 and executed by microprocessor 54 with input received from sensor terminals 70 and optionally electrode terminals 68 for detecting respiration events and for detecting obstructed inspiration.

Microprocessor 54 may be configured to execute software-implemented algorithms detecting inspiration and expiration phases of respiration and further perform processing of the blood pressure signal for determining metrics of inspiratory effort for detecting obstructed inspiration (or a lack of inspiratory effort). In some embodiments, IMD 10 is configured to derive a respiration signal from the blood pressure signal and determine the onset of breath cycles as generally described in commonly assigned U.S. patent application Ser. No. 12/262,277, hereby incorporated herein by reference in its entirety.

Respiration data may be stored for use in diagnosing or monitoring the patient or for determining the need for delivering or adjusting a therapy under control of the operating system. The operating system includes associated memory 56 for storing a variety of operating algorithms and parameter values that are used by microprocessor 54. The memory 56 may also be used for storing data compiled from sensed physiological signals and/or relating to device operating history for telemetry out on receipt of a retrieval or interrogation instruction. Microprocessor 54 may respond to the respiration data by altering a therapy, triggering data storage, enabling other sensors for acquiring physiological data, or triggering alert 74 to generate an alert signal to the patient or a caregiver that a serious condition has been detected that may require medical intervention. Data relating to respiration may be stored in memory 56 for later retrieval.

IMD 10 further includes telemetry circuitry 64 and antenna 65. Programming commands or data are transmitted during uplink or downlink telemetry between IMD telemetry circuitry 64 and external telemetry circuitry included in a programmer or monitoring unit as shown in FIG. 1.

Figure 3:
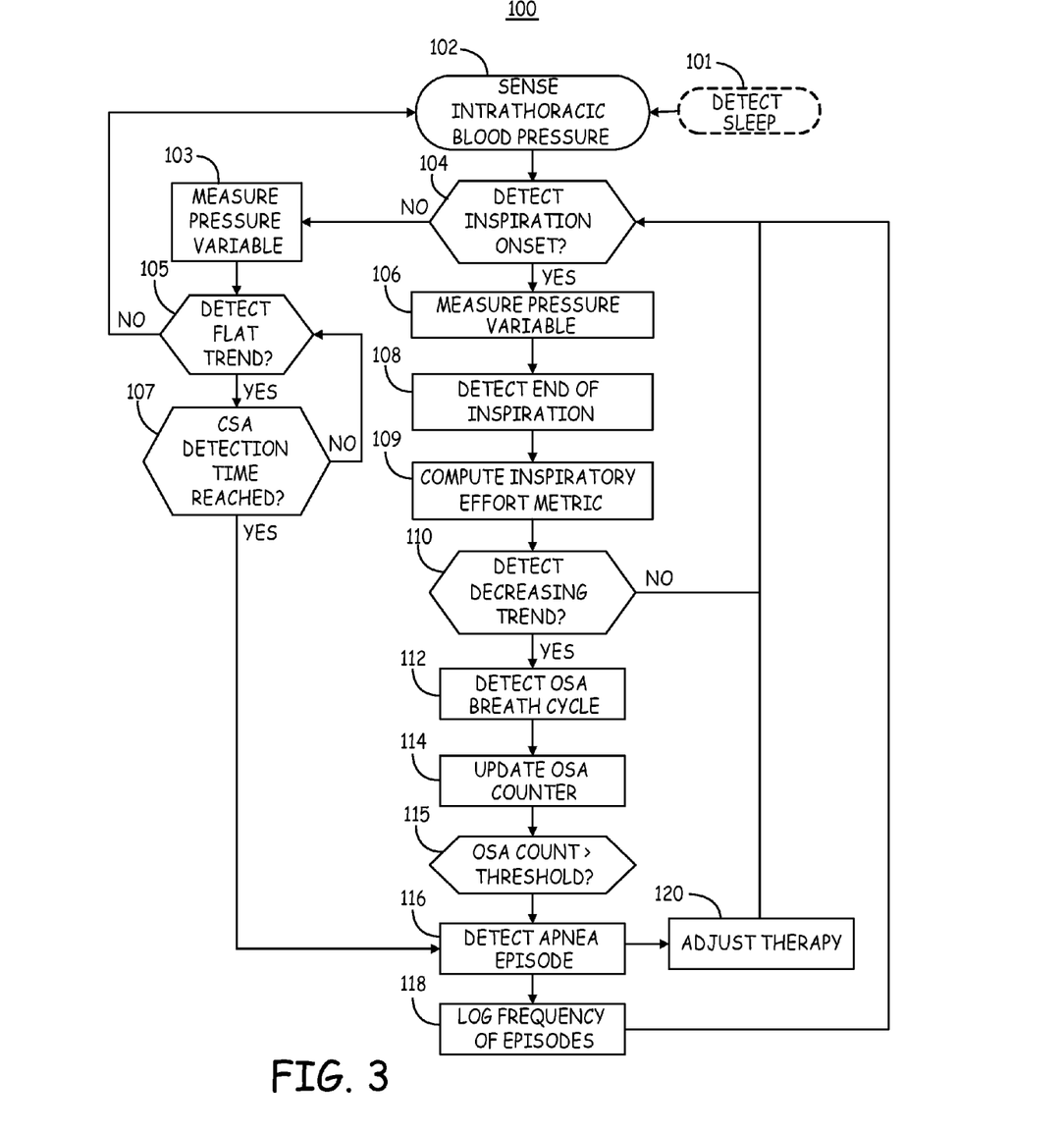
FIG. 3 is a flowchart of one embodiment of a method for measuring inspiratory effort using an intrathoracic blood pressure signal.

FIG. 3 is a flowchart 100 of one embodiment of a method for detecting obstructed inspiration using an intrathoracic blood pressure signal. Flowchart 100 is intended to illustrate the functional operation of a medical device system, and should not be construed as reflective of a specific form of software or hardware necessary to practice embodiments described herein. It is believed that the particular form of software, firmware and/or hardware will be determined primarily by the particular system architecture employed in the device system and by the particular detection and therapy delivery methodologies employed by the implantable device. Providing software, firmware and/or hardware to accomplish the operations described herein in the context of any modern implantable device system, given the disclosure herein, is within the abilities of one of skill in the art.

Methods described in conjunction with the flowchart 100 may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 102, an intrathoracic blood pressure signal is sensed using a transvenous pressure sensor. At block 104, the onset of the inspiration phase of a breath cycle is detected. Inspiration onset may be detected in a number of ways. In one embodiment, the onset of inspiration is detected using a pressure-derived respiration signal as generally described in the above-incorporated U.S. patent application Ser. No. 12/262,277. Briefly, a heart-rate dependent filtering method is used to derive a respiration signal from a blood pressure signal and an adjustable threshold can be used for detecting inspiration and expiration cycles. By using the same pressure signal for detecting inspiration onset and for measuring inspiratory effort, additional sensors are not needed and signal processing may be more efficient. However other methods may be used for detecting the onset of inspiration such as a using a thoracic impedance signal, using the low frequency respiration component of other signals such as an ECG signal, a motion sensor on the diaphragm, or the like.

After detecting inspiration onset, a blood pressure variable is measured from the pressure signal at block 106 during the inspiration phase. In one embodiment, diastolic blood pressure is measured beat-by-beat until the end of the inspiration phase is detected at block 108. The end of the inspiration phase may be based on a threshold crossing or other criteria applied to a respiration signal to detect the onset of the next expiration phase. Any of the signals described above for detecting the onset of inspiration may also be used for detecting the end of inspiration (or onset of expiration).

In other embodiments, a peak systolic pressure, mean pressure or other pressure measurement may be taken during each cardiac cycle during the inspiration phase at block 106. At block 109, a metric of inspiratory effort is computed using the inspiration phase pressure measurements. Various metrics of inspiratory effort that may be computed using pressure measurement obtained during an inspiration phase are described in conjunction with FIG. 4 below.

At block 110, comparative analysis of the inspiratory metric is performed to determine if an increase in inspiratory effort associated with an obstructed airway is detected. In general, the blood pressure measurement will decrease from beat-to-beat during the inspiration phase. This decrease becomes greater or exaggerated when inspiratory effort increases due to airway obstruction. As such, any evidence of a greater than normal decreasing trend in the blood pressure measurement during the inspiration phase can be detected as evidence of obstructed inspiration. For example, if the inspiratory effort metric crosses an obstructed inspiration detection threshold, an obstructed breathing cycle is detected at block 112. In an application for monitoring for sleep apnea, when the obstructed breathing cycle is detected during sleep, the obstructed cycle may be referred to as an "OSA breath cycle".

At block 114, a count of detected OSA breath cycles may be updated such that, if a threshold number of OSA breath cycles are counted (block 115), an episode of OSA is detected at block 116. The duration of the episode can then be measured in units of time or number of breathing cycles. At block 118 the duration or frequency of detected OSA episodes may be logged or an OSA burden may be computed as the amount of time or number of breath cycles that the patient experiences OSA over a 24-hour period, over one week, over a detected period of sleep or another monitoring period. Other data, such as respiration rate, heart rate, time of day, blood pressure, etc. may be recorded with the detected OSA episode in the memory of the IMD for transmitting to an external device in the form of a diagnostic report, which may be displayed or printed for clinician review.

The process shown in FIG. 3 may further include detection of CSA allowing for discrimination between OSA and CSA episodes. If inspiration onset is not detected at block 104, a timer may be started to determine if a central sleep apnea detection time is reached at block 107 before an inspiration phase is detected. Optionally, the diastolic pressure, systolic pressure, mean pressure or any other pressure variable used to determine a metric of inspiratory effort may also be measured at block 103. A flat trend in the pressure variable between cardiac cycles is detected at block 105. A flat response, or minimally changing response, of the pressure measurement from beat-to-beat reflects an absence of respiratory oscillations in the pressure signal and is evidence of a lack of inspiratory effort, e.g. as associated with CSA. A minimal pressure measurement change from beat-to-beat may reflect shallow breathing associated with hypopnea, which may not meet inspiration onset detection criteria applied at block 104.

As such, if the change in the pressure variable from beat-to-beat is below a predetermined threshold (block 105), and a CSA detection time is reached (block 107), a CSA (or hypopnea) episode is detected at block 116. The frequency or burden of CSA/hypopnea episodes may be logged in a diagnostic report separately from OSA episodes at block 118. A different therapy response may be provided at block 120 in response to a CSA detection as compared to an OSA detection. For example, phrenic nerve stimulation may be provided in response to detecting CSA or hypopnea to restore inspiration.

It is recognized that in some embodiments, the method shown in flowchart 100 may further include steps for detecting the onset of sleep, as indicated at block 101, such that the OSA detection method is performed only when the patient is likely to be asleep. Sleep detection may be based on a programmed time of day when the patient is expected to be asleep. Other sleep detection methods may utilize cardiac, respiration, posture, activity or other physiological signals for detecting when a patient is asleep and/or when a patient is awake for enabling and disabling, respectively, the OSA detection method. While not explicitly shown in FIG. 3, it is recognized that detection of the patient waking up may cause the method to be disabled until sleep is again detected.

In some embodiments, the method shown in flowchart 100 is implemented in a monitoring device used for acquiring diagnostic/prognostic data without therapy delivery capabilities. OSA data acquired by the device is stored and available for transmission to an external device for review by a clinician. Such data is valuable to a clinician in diagnosing OSA and selecting a treatment plan.

In other embodiments, the implanted medical device may be capable of delivering a therapy or in communication with another therapy delivery device. As such, it is further contemplated that upon detecting an obstructed inspiration phase or an episode of OSA an automated therapy may be adjusted or delivered at block 120. The therapy may be intended to treat the OSA, such as enabling a CPAP machine or adjusting positive airway pressure applied by the CPAP machine. Another OSA therapy that may be controlled in response to detecting an obstructed inspiration phase or episode of OSA includes electrical stimulation of upper airway muscles.

Alternatively or additionally, a therapy intended to provide cardiac support may be adjusted or initiated at block 120. The decreased intrathoracic pressure associated with increased inspiratory effort increases venous return to the heart causing increased cardiac preload (increased end-diastolic volume of the heart). This increased preload can be deleterious to cardiac function, particularly in a heart failure patient. As such, detection of obstructed inspiration may trigger delivery of a cardiac therapy at block 120, which may be a cardiac pacing therapy, e.g., cardiac resynchronization therapy (CRT), vagal nerve stimulation, or drug delivery, to provide cardiac support to counteract the potential cardiac risks associated with OSA.

Figure 4:
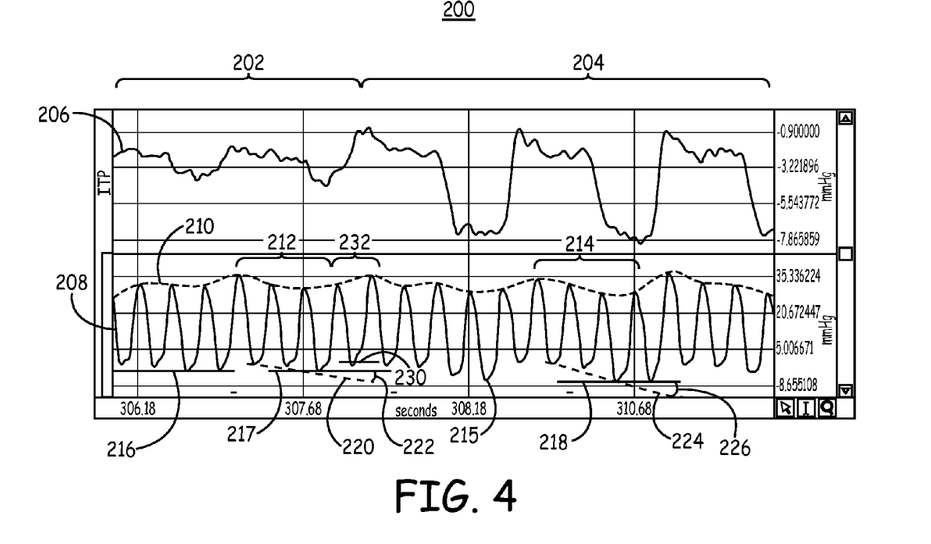
FIG. 4 is a time-based recording of intrathoracic pressure and right intraventricular pressure.

FIG. 4 is a time-based recording of intrathoracic pressure 206 and right intraventricular pressure 208. An initial period of normal respiration 202 is following by an episode of experimentally-induced obstructed airway inspiration 204, intended to mimic obstructive sleep apnea. A pressure-derived respiration signal 210 is shown, which can be obtained by applying heart-rate dependent filtering to the blood pressure signal 208. The pressure-derived respiration signal 210 may be used for detecting inspiration phases 212 and 214 and expiration phase 232 based on defined criteria. For example, inspiration and/or expiration phases may be detected based on respiration signal peak detections and/or threshold crossings.

Upon detecting the onset of an inspiration phase 212, the diastolic pressure may be measured during the inspiration phase 212. The diastolic pressure is the negative-going peak of the pressure signal, e.g. as shown at 215, and is typically a negative value. The diastolic pressure may be obtained for one or more cardiac cycles during the inspiration phase. The number of diastolic pressure measurements may depend on the heart rate and the inspiration phase duration. An average, median, or minimum (most negative) diastolic pressure measured during each inspiration phase may be computed. The measured diastolic pressure is used to determine a metric or inspiratory effort.

In some embodiments, the diastolic pressure measurement during inspiration is used directly as a metric of inspiratory effort. The diastolic pressure measurement may be compared to an obstructed inspiration detection threshold. Alternatively, the diastolic pressure measurement may be compared to previously acquired diastolic pressure measurements used to establish a baseline diastolic pressure.

In one embodiment, a baseline diastolic pressure is determined as a running average of diastolic pressure. A baseline diastolic pressure 216, represented as a running average of diastolic pressures, may be determined during normal respiration 202 when the patient is known to be awake or may be a long-term running average of all measurements. The baseline diastolic pressure 216 may be compared to minimum diastolic pressures 217 and 218 measured during inspiration phases 212 and 214, respectively. If the minimum diastolic pressure during an inspiration phase is less than the baseline diastolic pressure 216 by more than a predefined amount, for example more than 20% or another threshold amount less than the baseline, an OSA breath cycle is detected. In the example shown, the minimum diastolic pressure 217 during normal inspiration phase 212 is approximately equal the running baseline 216. The minimum diastolic pressure 218 during inspiration phase 214 is significantly less than the baseline 216 resulting in detection of an obstructed inspiration breathing cycle.

In an alternative embodiment, a decreasing slope 224 defined by diastolic pressure measurements obtained during an inspiration phase 214 is compared to predefined threshold or a previously measured slope 220. The slope 224 defined by the diastolic pressure measurements for at least two cardiac cycles during the inspiration phase 214 may be referred to as the right ventricular inspiratory slope (RVIS). The RVIS may be computed between consecutive diastolic pressure measurements or between an earliest-occurring diastolic pressure measurement after or just prior to detecting an inspiration phase onset and a subsequent diastolic pressure measurement made during the inspiration phase. For example, an earliest occurring pressure measurement and a minimum (most negative) diastolic pressure measurement during the inspiration phase may be selected for computing the RVIS.

Alternatively an angle 226 of the slope 224 relative to a flat baseline may be compared to an angle 222 of a baseline slope 220 relative to a flat baseline. With increased inspiratory effort due to OSA 204, the intrathoracic pressure 206 significantly decreases during the inspiration phase compared to during normal respiration 202. This decrease in intrathoracic pressure results in a significant decrease in diastolic blood pressure during an OSA inspiration phase 214 as compared to a normal inspiration phase 212. Thus the slope 224 and the angle 226 during an obstructed inspiration phase 214 will increase relative to the slope 220 and angle 222 during a non-obstructed inspiration phase 212. Thus RVIS 224 or its associated angle 226 may be computed as metrics of inspiratory effort. The increase in RVIS 224 or the angle 226 represents an increase in inspiratory effort associated with obstructed inspiration. The inspiratory slope may be computed for other intrathoracic blood pressure signals and is not limited to derivation from a right ventricular blood pressure signal.

In another embodiment, a diastolic pressure 230 may be measured during expiration 232 so that a difference between expiration phase diastolic pressure 230 and inspiration phase diastolic pressure 218 may be computed as a metric of inspiratory effort. The expiration phase diastolic pressure 230 may be measured as a running average of multiple expiration phases or measured during an expiration phase immediately preceding or immediately following a single inspiration phase. A comparative analysis of the expiration-inspiration diastolic pressure difference may then be used to discriminate between non-obstructed and obstructed inspiration phases. Other expiration-inspiration pressure measurement differences may be computed from the pressure waveform by using systolic pressures, mean pressures, peaks of a pressure-derived respiration signal 210, or other measurements computed from the intrathoracic blood pressure signal during cardiac cycles corresponding to a detected expiration phase and during cardiac cycles corresponding to a detected inspiration phase.

The example measurements illustrated in FIG. 4 require measurements of diastolic pressure. It is recognized that alternative embodiments may employ measurements of systolic pressure and/or mean blood pressure. As such, the slope or decreasing trend in systolic pressure, mean pressure, or other beat-by-beat pressure measurements may be used to detect increased inspiratory effort crossing an OSA detection threshold (or detection threshold depending on the monitoring application). In general, any blood pressure measurement made during the inspiration phase of the respiration cycle can be used if the measurement demonstrates the characteristic change in pressure that occurs during obstructed inspiration, i.e. an enhancement or exaggeration of the decreasing trend of the blood pressure measurement during obstructed inspiration as compared to the decreasing trend of the same blood pressure measurement during normal inspiration.

Figure 5:
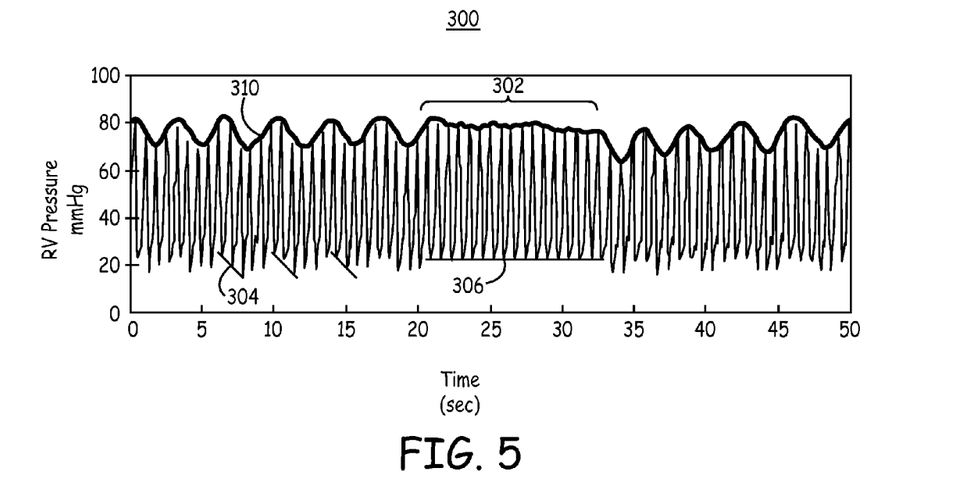
FIG. 5 is a right ventricular blood pressure recording during an episode of central sleep apnea.

FIG. 5 is a right ventricular blood pressure recording 300 during an episode of CSA 302. Prior to (and after) the CSA episode 302 the RVIS 304 is seen to be regular and substantially unchanged between inspiration cycles. A pressure-derived respiration signal 310 clearly shows oscillations corresponding to breath cycles allowing detection of the onset of inspiration phases and the RVIS, or another pressure trend during the inspiration phases, to be measured.

During the CSA episode 302, the pressure-derived respiration signal 310 becomes relatively flat due to lack of inspiratory effort. No inspiration phases are detected. Since inspiration phases are not being detected, pressure trend measurements during inspiration phases cannot be performed. Beat-to-beat pressure measurements, however, can be made and will exhibit a generally flat response since the oscillatory effect of respiration is absent or minimal during CSA or hypopnea. For example, beat-to-beat diastolic pressure measurements 306 show little variation. This trend of little or no change between beat-to-beat pressure measurements extending for a predetermined period of time, e.g. for at least approximately 10 seconds, is evidence of CSA (or hypopnea). As shown in FIGS. 4 and 5, an intrathoracic blood pressure measurement can be used to detect and discriminate between OSA and CSA, allowing appropriate diagnosis and therapy selections to be made.

Thus, a system and method for respiration monitoring have been presented in the foregoing description with reference to specific embodiments. It is appreciated that various modifications to the referenced embodiments may be made without departing from the scope of the disclosure as set forth in the following claims.

The invention claimed is:

1. A method for detecting obstructed inspiration for use in an implantable medical device system, comprising:
   receiving by a processor of an implantable medical device a blood pressure signal from an implantable pressure sensor;
   receiving by the processor a respiration signal;
   detecting an onset and an end of a phase of respiratory inspiration from the respiration signal;
   detecting the pressure signal occurring only between the onset and the end of the detected inspiration phase;
   measuring a trend in the pressure signal detected during the inspiration phase;
   detecting an obstructed breath cycle for the inspiration phase in response to the trend;
   updating a counter in response to detecting the obstructed breath cycle; and
   enabling the processor to detect an obstructive sleep apnea episode in response to the counter reaching a detection threshold number of obstructed breath cycles.

2. The method of claim 1 wherein measuring the trend comprises measuring a decreasing diastolic pressure.

3. The method of claim 1 wherein measuring the trend comprises comparing a pressure measured from the pressure signal during the inspiration phase and a previous pressure measurement obtained during a previous inspiration phase.

4. The method of claim 1 wherein measuring the trend comprises measuring an inspiratory slope between a first pressure measurement and a second pressure measurement, the first and second pressure measurements occurring on two different cardiac cycles during the same inspiration phase.

5. The method of claim 4 wherein detecting the obstructed inspiration further comprises comparing the inspiratory slope to a previously measured inspiratory slope.

6. The method of claim 1 wherein measuring the trend in the pressure signal comprises:

measuring a first blood pressure variable during the inspiration phase;
detecting an expiration phase from the respiration signal;
measuring a second blood pressure variable during the expiration phase; and
computing a difference between the first blood pressure variable and the second blood pressure variable.

7. The method of claim 1 further comprising:
setting an obstructive sleep apnea threshold;
counting a number of consecutive inspiration phases detected as obstructed inspiration; and
detecting an episode of obstructive sleep apnea in response to the number exceeding the threshold.

8. The method of claim 7 further comprising storing one of a frequency and a duration of detected obstructive sleep apnea episodes.

9. The method of claim 1 further comprising adjusting a therapy in response to detecting the obstructed inspiration, the therapy comprising one of a sleep apnea therapy and a cardiac therapy.

10. The method of claim 1 further comprising:
when an inspiration phase is not detected, measuring a blood pressure on each cardiac cycle of the blood pressure measurement;
determining a beat-to-beat change in the blood pressure measurement;
detecting a lack of inspiratory effort in response to the beat-to-beat change in the blood pressure measurement being less than a threshold; and
detecting an episode of central sleep apnea in response to the detected lack of inspiratory effort.

11. An implantable medical device, comprising:
a pressure sensor for sensing a blood pressure signal;
means for monitoring a respiration signal; and
a processor receiving the blood pressure signal and configured to:
determine an onset and an end of a phase of respiratory inspiration from the respiration signal;
detect the pressure signal occurring only between the onset and the end of the detected inspiration phase;
measure a trend in the pressure signal detected during the inspiration phase;
detect an obstructed breath cycle for the inspiration phase in response to the trend, update a counter in response to detecting the obstructed breath cycle; and detect an obstructive sleep apnea episode in response to the counter reaching a detection threshold number of obstructed breath cycles.

12. The device of claim 11 wherein measuring the trend comprises measuring a decreasing diastolic pressure.

13. The device of claim 11 wherein measuring the trend comprises comparing a pressure measured from the pressure signal during the inspiration phase and a previous pressure measurement obtained during a previous inspiration phase.

14. The device of claim 11 wherein measuring the trend comprises measuring an inspiratory slope between a first pressure measurement and a second pressure measurement, the first and second pressure measurements occurring on two different cardiac cycles during the same inspiration phase.

15. The device of claim 14 wherein detecting the obstructed inspiration further comprises comparing the inspiratory slope to a previously measured inspiratory slope.

16. The device of claim 11 wherein measuring the trend in the pressure signal comprises:
measuring a first blood pressure variable during the inspiration phase;
detecting an expiration phase from the respiration signal;
measuring a second blood pressure variable during the expiration phase; and
computing a difference between the first blood pressure variable and the second blood pressure variable.

17. The device of claim 11 further comprising a memory storing an obstructive sleep apnea threshold;
wherein the processor is further configured to:
count a number of consecutive inspiration phases detected as obstructed inspiration; and
detect an episode of obstructive sleep apnea in response to the number exceeding the threshold.

18. The device of claim 17 wherein the processor is further configured to determine one of a frequency and a duration of obstructive sleep apnea episodes.

19. The device of claim 11 further comprising a therapy delivery module;
wherein the processor is further configured to adjust a therapy in response to detecting the obstructed inspiration, the therapy comprising one of a sleep apnea therapy and a cardiac therapy.

20. The device of claim 11 wherein the processor is further configured to:
measure a blood pressure on each cardiac cycle of the blood pressure measurement when an inspiration phase is not detected;
determine a beat-to-beat change in the blood pressure measurement;
detect a lack of inspiratory effort in response to the beat-to-beat change in the blood pressure measurement being less than a threshold; and
detect an episode of central sleep apnea in response to the detected lack of inspiratory effort.

21. A non-transitory computer-readable medium storing a set of instructions for detecting obstructed inspiration and causing a programmable processor included in an implantable medical device system to:
monitor a blood pressure signal;
monitor a respiration signal;
determine an onset and an end of a phase of respiratory inspiration from the respiration signal;
measure a trend in the pressure signal during the inspiration phase;
detect an obstructed breath cycle for the inspiration phase in response to the trend;
update a counter in response to detecting the obstructed breath cycle; and
detect an obstructive sleep apnea episode in response to the counter reaching a detection threshold number of obstructed breath cycles.

* * * * *